US00PP15234P3

(12) United States Plant Patent
Briant

(10) Patent No.: US PP15,234 P2
(45) Date of Patent: Oct. 12, 2004

(54) ***LONICERA NITIDA* PLANT NAMED 'BRILONI'**

(50) Latin Name: *Lonicera nitida*
Varietal Denomination: Briloni

(75) Inventor: André Briant, Saint-Barthelemy D'Anjou (FR)

(73) Assignee: Selection New Plant SARL, Le Luc en Provence (FR)

( * ) Notice: Subject to any disclaimer, the term of this patent is extended or adjusted under 35 U.S.C. 154(b) by 0 days.

(21) Appl. No.: 10/340,666

(22) Filed: Jan. 13, 2003

(65) Prior Publication Data

US 2004/0139509 P1 Jul. 15, 2004

(51) Int. Cl.[7] ..... A01H 5/00

(52) U.S. Cl. ..... Plt./226

(58) Field of Search ..... Plt./226

*Primary Examiner*—Anne Marie Grunberg
*Assistant Examiner*—June Hwu
(74) *Attorney, Agent, or Firm*—Burns, Doane, Swecker & Mathis, L.L.P.

(57) ABSTRACT

A new and distinct *Lonicera nitida* cultivar is provided that is a mutation of the 'Maigrün' cultivar (non-patented in the United States). Distinctive new foliage is formed that bears yellow-green coloration unlike that of the 'Maigrün' cultivar. A spreading growth habit is displayed and the plant performs well in a semi-shaped environment. The unusual foliage coloration combined with the other characteristics provides the horticultural industry with an distinctive ornamental plant for growing in pots or in the landscape.

2 Drawing Sheets

Botanical/commercial classification: *Lonicera nitida/ Lonicera* Plant.
Varietal denomination: cv. 'Briloni'.

SUMMARY OF THE INVENTION

The present invention comprises a new and distinct cultivar of *Lonicera nitida,* and hereafter is referred to by the cultivar name 'Briloni'. Plants of this species sometimes are called Box Honeysuckle.

A single plant possessing the characteristics of the new cultivar was discovered at Saint Barthélémy d'Anjou, Maine et Loire, France while growing among a block of plants of the 'Maigrün' cultivar (non-patented in the United States). The new cultivar of the present invention is believed to be a spontaneous mutation of the 'Maigrün' cultivar of unknown causation. I was attracted to the new cultivar primarily because of its distinctive foliage coloration that differed from that of the parental cultivar. Had the plant of this new cultivar not been discovered and preserved it would have been lost to mankind.

It was found that the new *Lonicera nitida* plant displays the following combination of characteristics:

(a) forms attractive new foliage that bears yellow-green coloration unlike that of the 'Maigrün' cultivar (non-patented in the United States), (b) possesses a spreading growth habit, (c) grows well in a semi-shaded environment, and (d) provides attractive ornamentation.

The new cultivar of the present invention can be readily distinguished from plants of the 'Maigrün' cultivar which forms new foliage that is consistently more green in coloration. Accordingly, the new foliage of the 'Briloni' cultivar is significantly more yellow and is often variegated yellow-green and green in coloration. Additionally, the 'Baggeen's Gold' cultivar (non-patented in the United States) while forming yellow foliage displays a significantly different growth habit. More specifically, the growth habit of the 'Baggeen's Gold' cultivar is upright and that of the new cultivar is spreading.

Asexual reproduction of the new cultivar by the use of cuttings as performed at Saint Barthélémy d'Anjou, Maine et Loire, France, has demonstrated that the characteristics of the new cultivar are firmly fixed and are retained through successive generations of asexual propagation.

The new cultivar well meets the needs of the horticultural industry and can be used to provide attractive ornamentation when grown in pots or in the landscape. Unlike some *Lonicera* plants, the new cultivar grows well in a semi-shaded environment.

BRIEF DESCRIPTION OF THE PHOTOGRAPHS

The accompanying photographs depict typical plants of the new cultivar while being grown outdoors at Saint Barthélémy d'Anjou, Maine et Loire, France, with color being shown as true as is reasonably possible in color illustrations of this character. Such plants were approximately four years of age and had been asexually reproduced through the use of cuttings.

Figure 1:
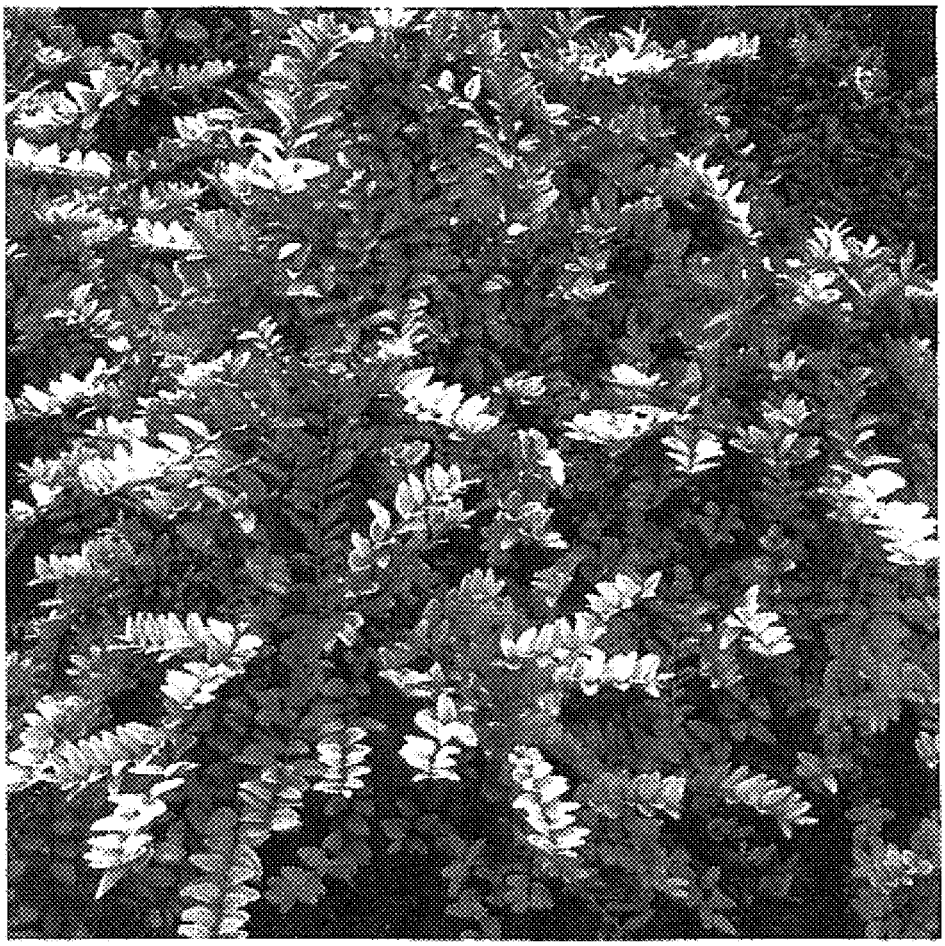

FIG. 1 provides a close view of the foliage where the distinctive yellow-green and green coloration of the newly formed foliage is shown.

Figure 2:
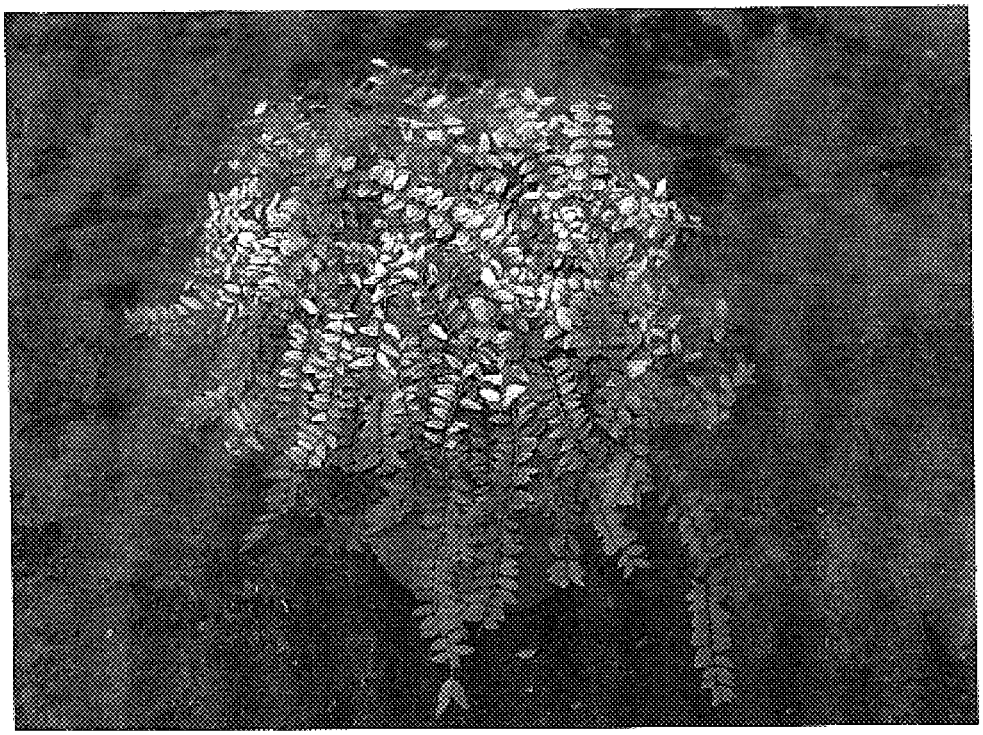

FIG. 2 provides an overall view of the compact spreading growth habit while grown in a pot. Variegated yellow-green and green foliage also is shown.

DETAILED DESCRIPTION

The plants were approximately four years of age and were observed during the autumn when grown outdoors at Saint Barthélémy d'Anjou, Maine et Loire, France. Such plants had been asexually reproduced by the use of cuttings and had undergone some pruning. Color terminology is with reference to The R.H.S. Colour Chart of The Royal Horticultural Society, London.

Origin: Spontaneous mutation of the 'Maigrün' cultivar (non-patented in the United States).

Plant:

*Form.*—Spreading if left untrimmed. Pruning yields a nicely-branched rounded form.

*Height.*—Approximately 80 cm on average.

*Width.*—Approximately 100 cm on average.

Branches:

*Configuration.*—Substantially ovoid in cross-section.

*Texture.*—Glabrous.

*Length.*—Typically approximately 40 to 50 cm.

*Diameter.*—Approximately 0.7 cm.

*Color.*—Young Stems: Greyed-Orange Group 177A and 177B. Adult Wood: Greyed-Orange Group 177A and 177B.

Foliage:

*Length.*—Approximately 1.4 cm on average.

*Width.*—Approximately 0.7 cm on average.

*Arrangement.*—Opposite.

*Margin.*—Entire.

*Apex.*—Obtuse.

*Base.*—More or less rounded and abruptly extends downward as a short triangle.

*Texture.*—Glabrous.

*General appearance.*—Dense.

*Color.*—New Foliage: Upper Surface: Commonly variegated between near Yellow-Green Group 154A to 154D and Yellow-Green Group 146C. Under Surface: Commonly variegated between near Yellow-Green Group 154A to 154D and Yellow-Green 146C. Mature Foliage: Upper Surface: Generally possesses more green coloration than the newly formed foliage and includes variegation between near Yellow-Green Group 154A to 154D and Yellow-Green Group 146C. Under Surface: Generally possesses more green coloration than the newly formed foliage and includes variegation between near Yellow-Green Group 154A to 154D and Yellow-Green Group 146C.

*Petiole.*—Approximately 0.1 cm in length on average.

Inflorescence:

*Time of flowering.*—May.

*Bloom period.*—Approximately three weeks on average.

*Type.*—Inconspicuous.

*Size.*—Commonly approximately 10 to 12 mm in length and approximately 3 to 4 mm in diameter.

*Configuration.*—Tubular, typical of the *nitida* species, with the petal number and texture being typical of such species.

*Color.*—Creamy white and near Yellow Group 10D.

*Stamen.*—Five in number, approximately 6 mm in length, and near Yellow Group 11D in coloration.

*Pistil.*—One in number, approximately 10 mm in length, and near Yellow Group 11D in coloration.

*Calyx.*—Near Yellow Group 11C and 11D in coloration.

*Hips.*—Substantially round, approximately 0.5 cm in diameter, somewhat translucent, and near Violet Group 85A to 85C in coloration.

During observations to date no disease problems have been observed. Also, plants of the new variety have not been harmed by insects during observations to date.

The new variety is well adapted for growing in U.S.D.A. Hardiness Zone Nos. 6 and 7.

Plants of the new 'Briloni' variety have not been observed under all possible environmental conditions to date. Accordingly, it is possible that the phenotypic expression may vary somewhat with changes in light intensity and duration, cultural practices, and other environmental conditions.

I claim:

1. A new and distinct cultivar *Lonicera nitida* plant that exhibits the following combination of characteristics:

(a) forms attractive new foliage that bears yellow-green coloration unlike that of the 'Maigrün' cultivar (non-patented in the United States), (b) possesses a spreading growth habit, (c) grows well in a semi-shaded environment, and (d) provides attractive ornamentation; substantially as illustrated and described.

* * * * *